United States Patent
Dehmlow et al.

(10) Patent No.: US 7,897,815 B2
(45) Date of Patent: Mar. 1, 2011

(54) HEXAFLUOROISOPROPANOL DERIVATIVES

(75) Inventors: Henrietta Dehmlow, Grenzach-Wyhlen (DE); Bernd Kuhn, Liestal (CH); Raffaello Masciadri, Basel (CH); Narendra Panday, Basel (CH); Hasane Ratni, Habsheim (FR); Matthew Blake Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/556,598

(22) Filed: Sep. 10, 2009

(65) Prior Publication Data

US 2010/0004297 A1    Jan. 7, 2010

Related U.S. Application Data

(60) Continuation of application No. 11/821,067, filed on Jun. 20, 2007, now abandoned, which is a division of application No. 11/168,622, filed on Jun. 27, 2005, now Pat. No. 7,259,178.

(30) Foreign Application Priority Data

Jun. 28, 2004    (EP)   ................ 041030065

(51) Int. Cl.
     *C07C 211/14*      (2006.01)
     *A61K 31/135*      (2006.01)
(52) U.S. Cl. ................. 564/355; 514/653
(58) Field of Classification Search .......... 564/355; 514/653
See application file for complete search history.

(56) References Cited

U.S. PATENT DOCUMENTS

| | | | | |
|---|---|---|---|---|
| 6,316,503 B1 * | 11/2001 | Li et al. | ............ | 514/604 |
| 6,900,244 B2 * | 5/2005 | Van Camp et al. | ............ | 514/538 |
| 7,259,178 B2 * | 8/2007 | Dehmlow et al. | ............ | 514/374 |
| 7,608,721 B2 * | 10/2009 | Dehmlow et al. | ............ | 548/235 |

FOREIGN PATENT DOCUMENTS

| | | |
|---|---|---|
| WO | WO 03/090732 | 11/2003 |
| WO | WO 03/099769 | 12/2003 |
| WO | WO 03099769 | * 12/2003 |

OTHER PUBLICATIONS

Wilkerson et al. (European Journal of Medicinal Chemistry (1992), 27(6), 595-610).*
Willy et al., Genes Dev. 1995, 9:1033-45.
Song et al., Proc Natl Acad Sci USA.1994, 91:10809-13.
Miller NE., Lipids 1978,13:914-9.
Gordon et al., Am J Med. 1977, 62:707-14.
Lund et al., Arterioscler. Thromb. Vasc. Biol. 2003, 23:1169-77.
Joseph and Tontonoz, Curr. Opin. Pharmacol. 2003, 3:192-7.
Cao et al., J Biol Chem. 2003, 278:1131-6.

* cited by examiner

*Primary Examiner*—Robert Havlin
(74) *Attorney, Agent, or Firm*—George W. Johnston; Dennis P. Tramaloni; Samuel H. Megerditchian

(57) ABSTRACT

The invention is concerned with novel hexafluoroisopropanol derivatives of formula (I)

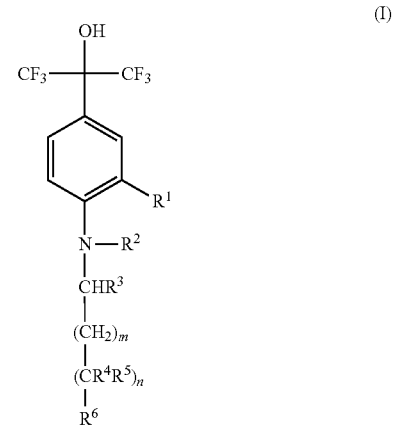

wherein $R^1$ to $R^6$, m and n are as defined in the description and in the claims, as well as physiologically acceptable salts and esters thereof. These compounds bind to LXR alpha and LXR beta and can be used as medicaments.

15 Claims, No Drawings

HEXAFLUOROISOPROPANOL DERIVATIVES

PRIORITY TO RELATED APPLICATIONS

This application is a continuation of application Ser. No. 11/821,067, filed Jun. 20, 2007, which is a division of U.S. application Ser. No. 11/168,622, filed Jun. 27, 2005, now patented, which claims the benefit of European Application No. 04103006.5, filed Jun. 28, 2004. The entire contents of the above-identified application is hereby incorporated by reference.

FIELD OF THE INVENTION

The invention is directed to novel hexafluoroisopropanol derivatives of the formula (I):

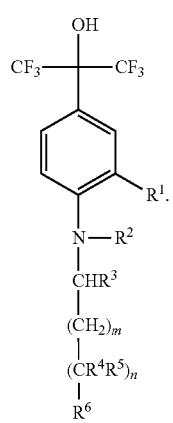

(I)

Further, the invention is concerned with a process for the manufacture of the above compounds, pharmaceutical preparations which contain such compounds as well as the use of these compounds for the production of pharmaceutical preparations.

All documents cited or relied upon below are expressly incorporated herein by reference.

BACKGROUND OF THE INVENTION

Liver-X-Receptors (LXRs) are members of the nuclear hormone receptor superfamily. The LXRs are activated by endogenous oxysterols and regulate the transcription of genes controlling multiple metabolic pathways. Two subtypes, LXRalpha and LXRbeta, have been described (Willy et al., Genes Dev. 1995, 9:1033-45; Song et al., Proc Natl Acad Sci USA. 1994, 91:10809-13). LXRbeta is ubiquitously expressed, while LXRalpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs are also involved in glucose metabolism, cholesterol metabolism in the brain, cell differentiation, and inflammation.

At present, approximately half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978, 13:914-9). The protective function of HDL derives from its role in a process termed reverse cholesterol transport. HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon et al., Am J Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol>240 mg/dl is 37% in diabetic men and 44% in women. The rates for LDL-C>160 mg/dl are 31% and 44%, and for HDL-C<35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs would result in compounds with enhanced therapeutic potential, and as such, modulators of LXRs should improve the plasma lipid profile, and raise HDL-C levels (Lund et al., Arterioscler. Thromb. Vasc. Biol. 2003, 23:1169-77). LXRs are also known to control the efflux of cholesterol from the macrophage foam cell of the atherosclerotic lesion, and agonists of LXRs have been shown to be atheroprotective (Joseph and Tontonoz, Curr. Opin. Pharmacol. 2003, 3:192-7). Thus, modulators of LXRs would be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao et al., J Biol Chem. 2003, 278:1131-6). Thus LXR modulators can also show superior therapeutic efficacy on HDL-raising and atheroprotection, with additional effects on diabetes, compared to current therapies.

The novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment and prophylaxis of age-related and inherited (e.g. Stargardt's disease) forms of macular degeneration.

Other compounds that bind to and activate LXR alpha and LXR beta have previously been suggested (e.g.: WO 03/099769). However, there is still a need for new compounds with improved properties. The present invention provides the novel compounds of formula (I) which bind to LXR alpha and/or LXR beta. The compounds of the present invention unexpectedly exhibit improved pharmacological properties compared to the compounds known in the art, concerning e.g. metabolic stability, bioavailability and activity.

SUMMARY OF THE INVENTION

In an embodiment of the invention, provided is a compound of formula (I):

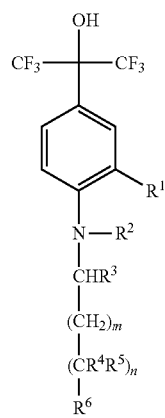

(I)

wherein
$R^1$ is hydrogen, halogen, or lower-alkyl;
$R^2$ is lower-alkyl, fluoro-lower-alkyl, cycloalkyl-lower-alkyl, or heterocyclyl-lower-alkyl;
$R^3$ is hydrogen, lower-alkyl, aryl, cycloalkyl, or heterocyclyl;

$R^4$ is hydrogen, hydroxy, lower-alkoxy, aryl-lower-alkoxy, or heterocyclyl-lower-alkoxy;
$R^5$ is hydrogen, lower-alkyl, aryl, or heterocyclyl;
$R^6$ is aryl, heterocyclyl, or

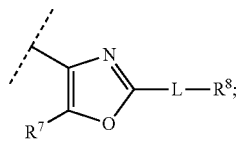

$R^7$ is lower-alkyl or fluoro-lower-alkyl;
$R^8$ is phenyl which is optionally substituted with 1 to 3 substituents selected from the group consisting of hydroxy, amino, halogen, lower-alkyl, fluoro-lower-alkyl, hydroxy-lower-alkyl, $R^9$—O—C(O)—, $R^{10}R^{11}NC(O)$—, $R^{12}$—O—C(O)-lower-alkyl, $R^{13}$—O—C(O)-hydroxy-lower-alkyl, $R^{14}R^{15}NC(O)$-lower-alkyl, $R^{16}R^{17}NC(O)$-hydroxy-lower-alkyl, lower-alkoxy, aryl-lower-alkoxy, $R^{18}$—O—C(O)-lower-alkoxy and $R^{19}R^{20}NC(O)$-lower-alkyoxy;
$R^9, R^{10}, R^{11}, R^{12}, R^{13}, R^{14}, R^{15}, R^{16}, R^{17}, R^{18}, R^{19}$ and $R^{20}$ independently from each other are hydrogen or lower-alkyl;
L is a single bond, lower-alkylene, or lower-alkenylene;
m is 0 to 3;
n is 0 or 1;
and pharmaceutically acceptable salts and esters thereof.

In another embodiment of the present invention, a process for the manufacture of compounds of formula (I) as defined above is provided, the process comprising the steps of:
a) reacting a compound of formula (II)

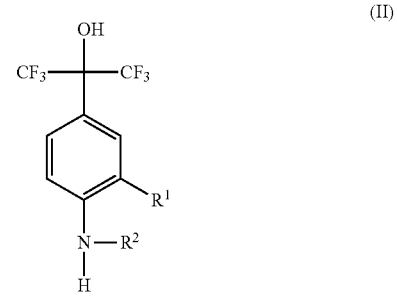

(II)

with a compound LG-CHR³—(CH₂)ₘ—(CR⁴R⁵)ₙ—R⁶, or
b) reacting a compound of formula (III)

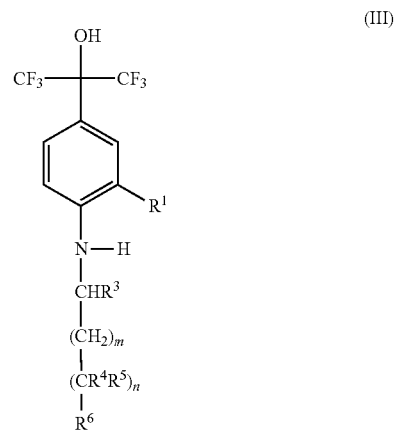

(III)

with a compound LG-R², wherein $R^1$, $R^2$, $R^3$, $R^4$, $R^5$, $R^6$, m and n are as defined in any of claims 1-23 and LG is a leaving group.

In a further embodiment of the present invention, provided is a pharmaceutical composition comprising a therapeutically effective amount of a compound of the formula I as defined above and a pharmaceutically acceptable carrier and/or adjuvant.

In a yet another embodiment of the present invention, a method is provided for the therapeutic and/or prophylactic treatment of diseases which are modulated by LXR alpha and/or LXR beta agonists, comprising the step of administering a therapeutically effective amount of a compound of the formula I as defined above to a patient in need thereof.

DETAILED DESCRIPTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted, e.g. by hydroxy. Such substituted lower-alkyl-groups are referred to as "hydroxy-lower-alkyl". Other possible optional substituents are e.g. halogen. Unsubstituted lower-alkyl groups are preferred.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H-CF_2$.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "thio-alkoxy" refers to the group R'—S—, wherein R' is an alkyl. The term "thio-lower-alkoxy" refers to the group R'—S—, wherein R' is a lower-alkyl.

The term "fluoro-lower-alkoxy" refers to the group R'—O—, wherein R' is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "alkenyl", alone or in combination with other groups, stands for a straight-chain or branched hydrocarbon residue comprising an olefinic bond and 2 to 20, preferably 2 to 16 carbon atoms, more preferably 2 to 10 carbon atoms. Lower-alkenyl groups as described below also are preferred alkenyl groups. The term "lower-alkenyl" refers to a straight-chain or branched hydrocarbon residue comprising an olefinic bond and 2 to 7, preferably 2 to 4 carbon atoms, such as e.g. 2-propenyl.

The term "alkynyl", alone or in combination with other groups, stands for a straight-chain or branched hydrocarbon residue comprising a triple bond and up to 20, preferably up to 16 carbon atoms. The term "lower-alkynyl" refers to a straight-chain or branched hydrocarbon residue comprising a triple bond and 2 to 7, preferably 2 to 4 carbon atoms, such as e.g. 2-propynyl. Lower-alkynyl groups can be substituted, e.g. by hydroxy.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups.

The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "alkenylene" refers to a straight chain or branched divalent hydrocarbon group comprising an olefinic bond and up to 20 carbon atoms, preferably up to 16 carbon atoms, more preferably up to 10 carbon atoms. Lower-alkenylene groups as described below also are preferred alkenylene groups. The term "lower-alkenylene" refers to a straight chain or branched divalent hydrocarbon group comprising an olefinic bond and up to 7, preferably up to 5, C-atoms. Straight chain alkenylene or lower-alkenylene groups are preferred.

The term "aryl" relates to the phenyl or naphthyl group, preferably the phenyl group, which can optionally be substituted by 1 to 5, preferably 1 to 3, substituents independently selected from the group consisting of lower-alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, and benzyloxy-lower-alkoxy. Preferred substituents are halogen and fluoro-lower-alkyl.

The term "heterocyclyl", alone or in combination, signifies a saturated, partially unsaturated or aromatic 5- to 10-membered, mono- or bicyclic heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, pyrrolyl, piperidinyl, piperazinyl, morpholinyl, thiomorpholinyl, pyrazoyl, triazolyl, tetrazolyl, isothiazolyl, imidazoyl (e.g. imidazol-4-yl and 1-benzyloxycarbonyl-imidazol-4-yl), benzoimidazolyl, pyrazoyl, pyridinyl, pyrazinyl, pyridazinyl, pyrimidinyl, hexahydro-pyrimidinyl, furyl, thienyl, thiazolyl, oxazolyl, isoxazolyl, indolyl (e.g. 2-indolyl), indazolyl, quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl), tetrahydropyranyl, quinoxalinyl, oxopyrrolidinyl and benzo[b]thiophenyl. Preferred are pyridinyl, thiazolyl and benzo[b]thiophenyl. A heterocyclyl group may also have a substitution pattern as described earlier in connection with the term "aryl". Aromatic heterocyclyl groups are preferred.

The term "leaving group" refers to a group that may be displaced by a nucleophile (e.g. a secondary amine). Typical leaving groups are e.g.: Cl, Br, I, O—SO$_2$-lower-alkyl (wherein O—SO$_2$—CH$_3$=OMs), O—SO$_2$-lower-fluoroalkyl (wherein O—SO$_2$—CF$_3$=OTf), O—SO$_2$-aryl (wherein wherein O—SO$_2$-ptolyl=OTs), O-(para-nitrophenyl).

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammoniumsalt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

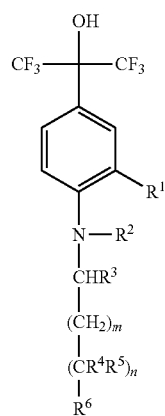

(I)

wherein
R$^1$ is hydrogen, halogen, or lower-alkyl;
R$^2$ is lower-alkyl, fluoro-lower-alkyl, cycloalkyl-lower-alkyl, or heterocyclyl-lower-alkyl;
R$^3$ is hydrogen, lower-alkyl, cycloalkyl, aryl, or heterocyclyl;
R$^4$ is hydrogen, hydroxy, lower-alkoxy, aryl-lower-alkoxy, or heterocyclyl-lower-alkoxy;
R$^5$ is hydrogen, lower-alkyl, aryl, or heterocyclyl;
R$^6$ is aryl, heterocyclyl, or

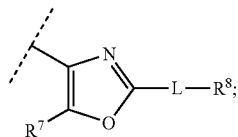

R$^7$ is lower-alkyl or fluoro-lower-alkyl;
R$^8$ is phenyl which is optionally substituted with 1 to 3 substituents selected from the group consisting of hydroxy, amino, halogen, lower-alkyl, fluoro-lower-alkyl, hydroxy-lower-alkyl, R$^9$—O—C(O)—, R$^{10}$R$^{11}$NC(O)—, R$^{12}$—O—C(O)-lower-alkyl, R$^{13}$—O—C(O)-hydroxy-lower-alkyl, R$^{14}$R$^{15}$NC(O)-lower-alkyl, R$^{16}$R$^{17}$NC(O)-hydroxy-lower-alkyl, lower-alkoxy, aryl-lower-alkoxy, R$^{18}$—O—C(O)-lower-alkoxy and R$^{19}$R$^{20}$NC(O)-lower-alkyoxy;
R$^9$, R$^{10}$, R$^{11}$, R$^{12}$, R$^{13}$, R$^{14}$, R$^{15}$, R$^{16}$, R$^{17}$, R$^{18}$, R$^{19}$ and R$^{20}$ independently from each other are hydrogen or lower-alkyl;
L is a single bond, lower-alkylene or lower-alkenylene;
m is 0 to 3;
n is 0 or 1;
and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, diastereomeric mixture or as optically pure compounds.

Preferred compounds of formula (I) as described above are those, wherein R$^1$ is hydrogen or halogen, preferably hydrogen or chlorine. Hydrogen and chlorine individually constitute preferred embodiments. Other preferred compounds of formula (I) as described above are those, wherein R$^2$ is lower-alkyl or fluoro-lower-alkyl, particularly ethyl or 2,2,2-trifluoro-ethyl. Ethyl and 2,2,2-trifluoroethyl individually constitute preferred embodiments.

Another preferred embodiment of the present invention relates to compounds of formula (I) as described above, wherein R$^3$ is hydrogen or aryl, particularly hydrogen or phenyl, especially hydrogen.

Other preferred compounds of formula (I) as described above are those, wherein R$^4$ is hydrogen or hydroxy. Compounds wherein R$^5$ is hydrogen are also preferred.

A further preferred embodiment of the present invention relates to compounds of formula (I) as described above, wherein R$^6$ is phenyl, pyridinyl, thiazolyl, or benzo[b]thiophenyl, which is optionally substituted with halogen. Each of the these groups can optionally be substituted with halogen, preferably phenyl or benzo[b]thiophenyl. Preferably, R$^6$ is phenyl, chloro-phenyl, pyridinyl, thiazolyl, or chloro-benzo[b]thiophenyl, more preferably phenyl.

Another preferred embodiment of the present invention relates to compounds as described above, wherein $R^6$ is

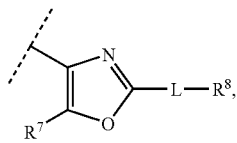

wherein $R^7$ is lower-alkyl; $R^8$ is phenyl which is optionally substituted with a substituent selected from the group consisting of halogen, fluoro-lower-alkyl, $R^9\leq O\text{—}C(O)\text{—}$, $R^{10}R^{11}NC(O)\text{—}$ and aryl-lower-alkoxy; $R^9$ is hydrogen or lower-alkyl; $R^{10}$ and $R^{11}$, independently from each other are hydrogen or lower-alkyl; L is a single bond, lower-alkylene, or lower-alkenylene. In such compounds, $R^7$ preferably is methyl. $R^8$ preferably is phenyl substituted with fluoro-lower-alkyl, halogen, carboxy, or (lower-alkyl)$_2$NC(O)—. More preferably, $R^8$ is 3-trifluoromethyl-phenyl, 3-chloro-phenyl, 4-carboxy-phenyl, or 4-(CH$_3$)$_2$NC(O)-phenyl. Furthermore, L preferably is a single bond.

In a preferred embodiment of the present invention, m is 0 to 2, more preferably m is 0. Compounds of formula (I) as described above, wherein n is 0 also constitute a preferred embodiment of the present invention.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of 2-[4-(Benzyl-ethyl-amino)-phenyl]-1,1,1,3,3,3-hexafluoro-propan-2-ol, 2-{4-[(2-Chloro-benzyl)-ethyl-amino]-phenyl}-1,1,1,3,3,3-hexafluoro-propan-2-ol, 2-{4-[(3-Chloro-benzyl)-ethyl-amino]-phenyl}-1,1,1,3,3,3-hexafluoro-propan-2-ol, 2-{4-[(4-Chloro-benzyl)-ethyl-amino]-phenyl}-1,1,1,3,3,3-hexafluoro-propan-2-ol, 2-[4-(Ethyl-phenethyl-amino)-phenyl]-1,1,1,3,3,3-hexafluoro-propan-2-ol, 2-[4-(Benzhydryl-ethyl-amino)-phenyl]-1,1,1,3,3,3-hexafluoro-propan-2-ol, 2-{4-[ethyl-(thiazol-4-ylmethyl)-amino]-phenyl}-1,1,1,3,3,3-hexafluoro-propan-2-ol, 2-{4-[ethyl-(pyridin-2-ylmethyl)-amino]-phenyl}-1,1,1,3,3,3-hexafluoro-propan-2-ol, 2-{4-[ethyl-(pyridin-3-ylmethyl)-amino]-phenyl}-1,1,1,3,3,3-hexafluoro-propan-2-ol, 2-{4-[ethyl-(pyridin-4-ylmethyl)-amino]-phenyl}-1,1,1,3,3,3-hexafluoro-propan-2-ol, 2-{4-[Benzyl-(2,2,2-trifluoro-ethyl)-amino]-phenyl}-1,1,1,3,3,3-hexafluoro-propan-2-ol, 2-{4-[(5-Chloro-benzo[b]thiophen-2-ylmethyl)-(2,2,2-trifluoro-ethyl)-amino]-phenyl}-1,1,1,3,3,3-hexafluoro-propan-2-ol, 2-{4-[Ethyl-(2-hydroxy-2-phenyl-ethyl)-amino]-phenyl}-1,1,1,3,3,3-hexafluoro-propan-2-ol, (R) 2-{4-[Ethyl-(2-hydroxy-2-phenyl-ethyl)-amino]-phenyl}-1,1,1,3,3,3-hexafluoro-propan-2-ol, (S) 2-{4-[Ethyl-(2-hydroxy-2-phenyl-ethyl)-amino]-phenyl}-1,1,1,3,3,3-hexafluoro-propan-2-ol, (R) 2-(4-{[2-(3-Chloro-phenyl)-2-hydroxy-ethyl]-ethyl-amino}-phenyl)-1,1,1,3,3,3-hexafluoro-propan-2-ol, 2-[4-(Benzyl-ethyl-amino)-3-chloro-phenyl]-1,1,1,3,3,3-hexafluoro-propan-2-ol, 2-{3-chloro-4-[ethyl-(thiazol-4-ylmethyl)-amino]-phenyl}-1,1,1,3,3,3-hexafluoro-propan-2-ol, 2-{4-[Benzyl-(2,2,2-trifluoro-ethyl)-amino]-3-chloro-phenyl}-1,1,1,3,3,3-hexafluoro-propan-2-ol, 2-{3-Chloro-4-[ethyl-(3-phenyl-propyl)-amino]-phenyl}-1,1,1,3,3,3-hexafluoro-propan-2-ol, 2-[3-Chloro-4-(ethyl-phenethyl-amino)-phenyl]-1,1,1,3,3,3-hexafluoro-propan-2-ol, 1,1,1,3,3,3-Hexafluoro-2-{4-[[5-methyl-2-(3-trifluoromethyl-phenyl)-oxazol-4-ylmethyl]-(2,2,2-trifluoro-ethyl)-amino]-phenyl}-propan-2-ol, 2-{4-[[2-(3-Chloro-phenyl)-5-methyl-oxazol-4-ylmethyl]-(2,2,2-trifluoro-ethyl)-amino]-phenyl}-1,1,1,3,3,3-hexafluoro-propan-2-ol, 2-(4-{Ethyl-[5-methyl-2-(3-trifluoromethyl-phenyl)-oxazol-4-ylmethyl]-amino}-phenyl)-1,1,1,3,3,3-hexafluoro-propan-2-ol, 2-(4-{[2-(3-Chloro-phenyl)-5-methyl-oxazol-4-ylmethyl]-ethyl-amino}-phenyl)-1,1,1,3,3,3-hexafluoro-propan-2-ol, 2-(3-Chloro-4-{ethyl-[5-methyl-2-(3-trifluoromethyl-phenyl)-oxazol-4-ylmethyl]-amino}-phenyl)-1,1,1,3,3,3-hexafluoro-propan-2-ol, 2-(3-Chloro-4-{[2-(3-chloro-phenyl)-5-methyl-oxazol-4-ylmethyl]-ethyl-amino}-phenyl)-1,1,1,3,3,3-hexafluoro-propan-2-ol, 2-(4-{[2-(3-Benzyloxy-phenyl)-5-methyl-oxazol-4-ylmethyl]-ethyl-amino}-phenyl)-1,1,1,3,3,3-hexafluoro-propan-2-ol, 2-(4-{[2-(4-Benzyloxy-phenyl)-5-methyl-oxazol-4-ylmethyl]-ethyl-amino}-phenyl)-1,1,1,3,3,3-hexafluoro-propan-2-ol, 3-[4-({Ethyl-[4-(2,2,2-trifluoro-1-hydroxy-1-trifluoromethyl-ethyl)-phenyl]-amino}-methyl)-5-methyl-oxazol-2-yl]-benzoic acid methyl ester, 4-[4-({Ethyl-[4-(2,2,2-trifluoro-1-hydroxy-1-trifluoromethyl-ethyl)-phenyl]-amino}-methyl)-5-methyl-oxazol-2-yl]-benzoic acid methyl ester, 3-[4-({Ethyl-[4-(2,2,2-trifluoro-1-hydroxy-1-trifluoromethyl-ethyl)-phenyl]-amino}-methyl)-5-methyl-oxazol-2-yl]-benzoic acid, 4-[4-({Ethyl-[4-(2,2,2-trifluoro-1-hydroxy-1-trifluoromethyl-ethyl)-phenyl]-amino}-methyl)-5-methyl-oxazol-2-yl]-benzoic acid, 3-[4-({Ethyl-[4-(2,2,2-trifluoro-1-hydroxy-1-trifluoromethyl-ethyl)-phenyl]-amino}-methyl)-5-methyl-oxazol-2-yl]-N-methyl-benzamide, 3-[4-({Ethyl-[4-(2,2,2-trifluoro-1-hydroxy-1-trifluoromethyl-ethyl)-phenyl]-amino}-methyl)-5-methyl-oxazol-2-yl]-N,N-dimethyl-benzamide, 3-[4-({Ethyl-[4-(2,2,2-trifluoro-1-hydroxy-1-trifluoromethyl-ethyl)-phenyl]-amino}-methyl)-5-methyl-oxazol-2-yl]-benzamide, 4-[4-({Ethyl-[4-(2,2,2-trifluoro-1-hydroxy-1-trifluoromethyl-ethyl)-phenyl]-amino}-methyl)-5-methyl-oxazol-2-yl]-N-methyl-benzamide, 4-[4-({Ethyl-[4-(2,2,2-trifluoro-1-hydroxy-1-trifluoromethyl-ethyl)-phenyl]-amino}-methyl)-5-methyl-oxazol-2-yl]-N,N-dimethyl-benzamide, 4-[4-({Ethyl-[4-(2,2,2-trifluoro-1-hydroxy-1-trifluoromethyl-ethyl)-phenyl]-amino}-methyl)-5-methyl-oxazol-2-yl]-benzamide, 2-{4-[(2-Benzyl-5-methyl-oxazol-4-ylmethyl)-ethyl-amino]-phenyl}-1,1,1,3,3,3-hexafluoro-propan-2-ol, 2-(4-{Ethyl-[5-methyl-2-((E)-styryl)-oxazol-4-ylmethyl]-amino}-phenyl)-1,1,1,3,3,3-hexafluoro-propan-2-ol, and
2-{4-[ethyl-(5-methyl-2-phenethyl-oxazol-4-ylmethyl)-amino]-phenyl}-1,1,1,3,3,3-hexafluoro-propan-2-ol, and pharmaceutically acceptable salts and esters thereof.

Particularly preferred compounds of formula (I) are those selected from the group consisting of
2-[4-(Benzyl-ethyl-amino)-3-chloro-phenyl]-1,1,1,3,3,3-hexafluoro-propan-2-ol,
2-{4-[Benzyl-(2,2,2-trifluoro-ethyl)-amino]-3-chloro-phenyl}-1,1,1,3,3,3-hexafluoro-propan-2-ol,
2-(4-{Ethyl-[5-methyl-2-(3-trifluoromethyl-phenyl)-oxazol-4-ylmethyl]-amino}-phenyl)-1,1,1,3,3,3-hexafluoro-propan-2-ol,
2-(4-{[2-(3-Chloro-phenyl)-5-methyl-oxazol-4-ylmethyl]-ethyl-amino}-phenyl)-1,1,1,3,3,3-hexafluoro-propan-2-ol,
4-[4-({Ethyl-[4-(2,2,2-trifluoro-1-hydroxy-1-trifluoromethyl-ethyl)-phenyl]-amino}-methyl)-5-methyl-oxazol-2-yl]-benzoic acid, and
4-[4-({Ethyl-[4-(2,2,2-trifluoro-1-hydroxy-1-trifluoromethyl-ethyl)-phenyl]-amino}-methyl)-5-methyl-oxazol-2-yl]-N,N-dimethyl-benzamide, and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises
a) reacting a compound of formula (II)

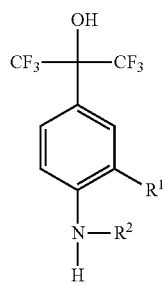

with a compound LG-CHR$^3$—(CH$_2$)$_m$—(CR$^4$R$^5$)$_n$—R$^6$, or b) reacting a compound of formula (III)

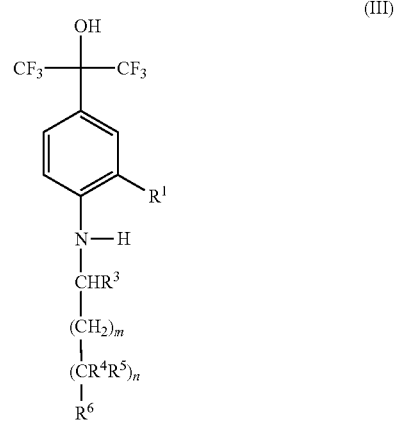

with a compound LG-R$^2$, wherein R$^1$, R$^2$, R$^3$, R$^4$, R$^5$, R$^6$, m and n are as defined above and LG is a leaving group.

The reaction of a compound of formula (II) with a compound LG-CHR$^3$—(CH$_2$)$_m$—(CR$^4$R$^5$)$_n$—R$^6$ or of a compound of formula (III) with a compound LG-R$^2$ can be performed under reaction conditions well known to the person skilled in the art. Such reactions can conveniently be carried out in a solvent such as e.g. DMF, THF, acetonitrile or acetone, optionally in the presence of a base such as e.g. DIPEA or K$_2$CO$_3$, at a suitable temperature, e.g. in the range of 20-200° C. Suitable leaving groups are well known in the art, e.g. halogenide (I, Br, Cl), triflate (OTf), mesylate (OMs), tosylate (OTs), or para-nitrophenolate.

The present invention also relates to compounds of formula (I) as defined above, when prepared by a process as described above.

The preparation of compounds of formula (I) as defined above, is illustrated in scheme 1.

Scheme 1

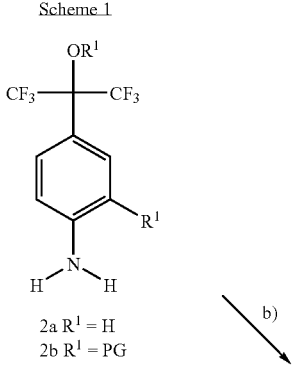

2a R$^1$ = H
2b R$^1$ = PG

-continued

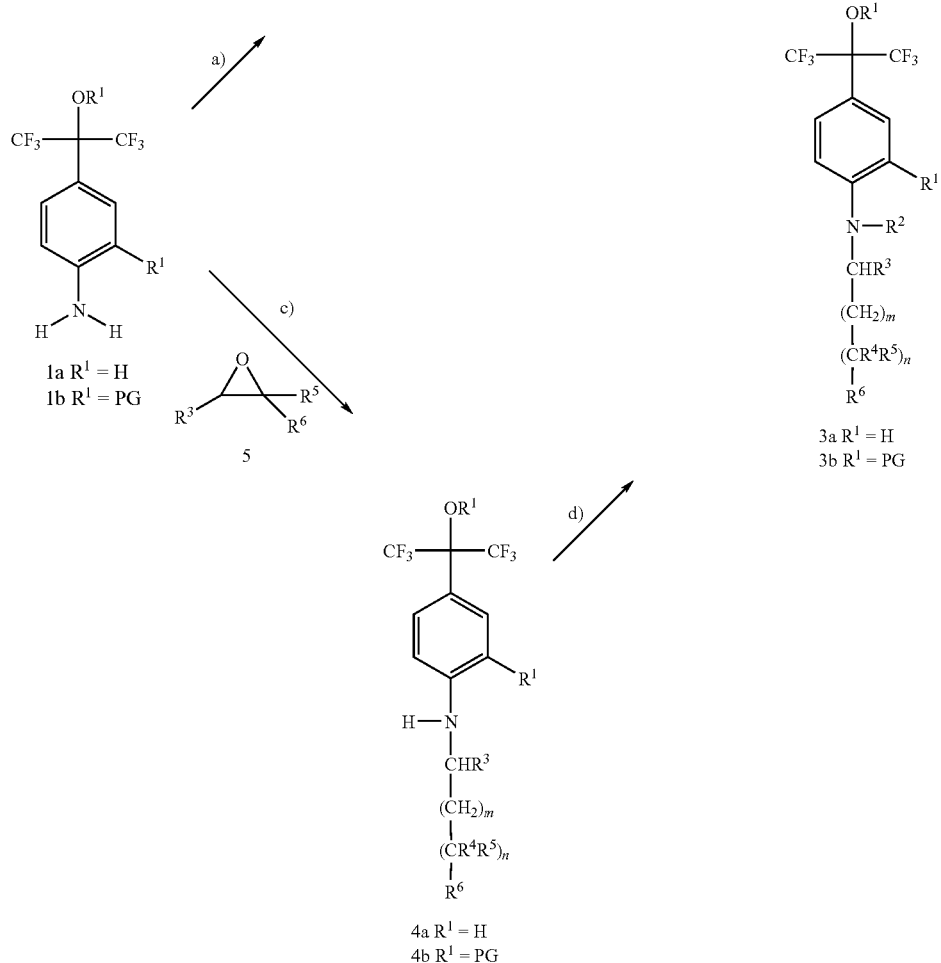

Treatment of an aniline 1a/b (PG=optional protective group) with LG-$R^2$ (wherein LG is a leaving group such as e.g. Cl, Br, I, MsO, TsO, or TfO) or with an acylating agent (a carboxylic acid anhydride or carboxylic acid chloride such as e.g. trifluoroacetic acid anhydride or benzoyl chloride) and subsequent reduction of the intermediate amide (e.g. with $BH_3$) leads to 2a/b (step a). Alternatively the formation of the intermediate amide may also be carried out by treatment of 1a/b with a carboxylic acid in presence of e.g. EDCI and HOBT or other typical reagents used for the formation of amides from carboxylic acids. The "$(CHR^3)(CH_2)_m(CR^4R^5)_nR^6$"-moiety is introduced in step b by reaction of 2a/b with a compound "LG-$(CHR^3)(CH_2)_m(CR^4R^5)_nR^6$". Alternatively, 2a/b can be treated with an acylating agent such as ClOC$(CH_2)_m(CR^4R^5)_nR^6$ in presence of a base or with a carboxylic acid HOOC$(CH_2)_m(CR^4R^5)_nR^6$ in the presence of e.g. EDCI and HOBT or other typical reagents used for the formation of amides from carboxylic acids. The resulting amide intermediate is reduced (e.g. with $BH_3$) to give derivatives with $R^3$=H. If 2a/b is treated with oxirane 5, optionally in the presence of a Lewis acid such as e.g. lithiumperchlorate or $ZnCl_2$ (in analogy to e.g.: Chini et al., J. Org. Chem., 1991, 56(20) 5939-5942; Duran Pachon et al., Tet. Lett., 2003, 44(32) 6025-6027), derivatives with m=0, n=1 and $R^5$=OH can be obtained. The methods used for the introduction of the "$(CHR^3)(CH_2)_m(CR^4R^5)_nR^6$"-moiety can also be applied to 1a/b (step c). The $R^2$-substituent is introduced subsequently into 4a/b according to the methods described above (step d). If step d is incompatible with functional groups present in 4a/b, these may be suitably protected prior to the introduction of $R^2$ and deprotected again thereafter. O-protected derivatives 1b may be obtained from 1a according to standard literature procedures used for the protection of alcohols (e.g. treatment of 1a with a silylating agent such as TESCl in the presence of a suitable base such as DBU). The conditions for the introduction of some O-protecting groups (e.g. O-benzylation with benzylbromide in presence of $K_2CO_3$) may require the prior protection of the amino group (e.g. by bocylation with $Boc_2O$) which is deprotected again after protection of the hydroxyl group. The removal of both O- and N-protecting groups—if desired or required—is carried out according to appropriate standard procedures generally known to those skilled in the art (e.g. N-debocylation in presence of TFA or N-desilylation with TBAF). Typical conditions for the introduction and removal of protecting groups may e.g. be found in "Protective Groups in Organic Synthesis" by T. W. Greene and P. G. M. Wuts, $2^{nd}$ Ed., 1991, Wiley N.Y.

Derivatives with $R^4$=hydroxy may be converted to derivatives with $R^4$=alkoxy, aryl-lower-alkoxy- and heterocyclyl-lower-alkoxy by treatment with a reagent LG-$R^{II}$, wherein $R^{II}$=loweralkyl, aryl-lower-alkyl or heterocyclyl-lower-alkyl in the presence of a base such as e.g. $K_2CO_3$. Derivatives with $R^4$=hydroxy and $R^5$=H may be oxidized (i.e. $CR^4R^5$ is converted to C=O) and treated with an organometal such as e.g. Li—$R^5$ or BrMg—$R^5$, wherein $R^5$ is lower-alkyl, aryl or heterocyclyl, to give derivatives with $R^4$=hydroxyl and $R^5$=lower-alkyl, aryl or heterocyclyl. If required, functional groups (e.g. present in $R^6$) incompatible with conditions used for the mentioned transformations of $R^4$ and $R^5$, may be suitably protected and deprotected again later (according to procedures given e.g. in "Protective Groups in Organic Synthesis" by T. W. Greene and P. G. M. Wuts, $2^{nd}$ Ed., 1991, Wiley N.Y.).

Derivatives 1a/b-4a/b with $R^1$=H may be converted to derivatives with $R^1$=halogen by treatment with a halogenating agent such as e.g. NCS, NBS, NIS, or N-fluoro-bis(trifluoromethylsulfonyl)amine. Derivatives 1a/b-4a/b with $R^1$=lower-alkyl may be obtained from derivatives with $R^1$=H in one step by Friedel-Crafts alkylation or in two steps by Friedel-Crafts acylation and subsequent reduction of the carbonyl group (e.g. by Wolff-Kishner- or Clemmensen-type reductions). Alternatively derivatives with $R^1$=Cl, Br, or I may be subjected to a metal-halogen-exchange reaction with e.g. BuLi or EtMgBr and then treated with an alkylating agent such as e.g. an alkyliodide. Instead of the alkylating agent, an aldehyde CHOalkyl may be used, leading to a derivative with $R^1$=1-hydroxyalkyl, that may be deoxygenated e.g. by hydrogenolysis in presence of a catalyst such as Pd/C, or by treatment with a reducing agent such as e.g. $BH_3.Me_2S$ or $Et_3Si$—H optionally in presence of an acid or Lewis acid such as e.g. TFA or $BF_3.OEt_2$ (e.g. in analogy to Pearlstein et al., Bioorg. and Med. Chem. Lett., 2003, 13, 1829-1835; Mewshaw et al., Bioorg. and Med. Chem. Lett., 2002, 12, 307-310; Sakagani et al., Synlett. 1996, 163-164). If necessary, sensitive functional groups present in 1a/b-4a/b, may be suitably protected prior to the preparation of derivatives with $R^1$=halogen or lower-alkyl and deprotected again at a later stage (e.g. according to procedures given in "Protective Groups in Organic Synthesis" by T. W. Greene and P. G. M. Wuts, $2^{nd}$ Ed., 1991, Wiley N.Y.).

A large number of compounds LG-$(CHR^3)(CH_2)_m(CR^4R^5)_nR^6$ in which $R^1$ to $R^6$, L, m, n, and LG are defined as above are commercially available. If not they may be prepared from a related commercially available starting material such as e.g. an alcohol HO—$(CHR^3)$—$(CH_2)_m(CR^4R^5)_nR^6$, an ester alkylOOC—$(CH_2)_m$—$(CR^4R^5)_nR^6$, or a carboxylic acid HOOC—$(CH_2)_m$—$(CR^4R^5)_nR^6$ according to standard literature procedures commonly known to those skilled in the art. If not commercially available, halogenides of the structure halogen-$(CHR^3)$—$(CH_2)_m(CR^4R^5)_nR^6$, wherein halogen=Cl or Br and either $R^3$=aryl or heterocyclyl or both m and n=0, may be prepared from e.g. $H_2CR^3$—$(CH_2)_m(CR^4R^5)_nR^6$ by treatment with NCS or NBS, respectively (e.g. Togo et al. Syn. Lett., 2003, 702-704). Oxiranes such as 5 may be prepared by treatment of 1-bisfunctionalized ethenes $C(HR^3)=C(R^5R^6)$ with a commonly used epoxidizing agent such as mCPBA (e.g. Durley et al., J. Med. Chem., 2002, 45, 18, 3891-3904; Tian et al., Org. Lett., 3, 12, 2001, 1929-1932). Many of the LG-$(CHR^3)(CH_2)_m(CR^4R^5)_nR^6$ wherein $R^3$, $R^4$, $R^5$=H, and $R^6$=heterocyclyl may be prepared according to literature procedures (e.g. Binggeli et al. WO200292084 and WO97019311, Bouillot et al. WO2004006922; Morita et al., JP09095482; Cynkowski et al., J. Chem. Soc. Chem. Commun., 1995, 2335-2336; Kodama et al., U.S. Pat. No. 6,472,386; Faul et al., Heterocycles, 2001, 55 (4), 689-704)

After preparation of 3a/b according to the synthetic descriptions above, functional groups present in $R^6$ may optionally be further derivatized. Examples for typical transformations of such functional groups are summarized below:

Benzyloxy is typically transformed to hydroxy; hydroxy to lower-alkoxy, $R^a$—O—C(O)-lower-alkoxy, and $R^aR^b$—NC(O)-lower-alkoxy; $R^a$—O—C(O)—, to hydroxymethyl and HO—C(O); HO—C(O) to $R^aR^bNC(O)$; hydroxymethyl to formyl, wherein the just mentioned functional groups may be present alone or form part of a larger functional group and wherein $R^a$ and $R^b$ independently from each other are hydrogen or lower alkyl. Procedures for these transformations are found in large number in literature and are commonly known to those skilled in the art.

Formyl may typically be transformed to 1-hydroxyalkyl, by addition of an alkylmagnesium halogenide or an alkyllithium. The formyl group may be derivatized to a 2-(lower-alkyl-O—C(O))-1-hydroxy ethyl group e.g. by Zn(0)-mediated addition of an α-bromoacetic acid ester (Reformatsky-reaction). If the 2-(loweralkyl-O—C(O))-1-hydroxy ethyl is formed from a formyl group directly attached to an aryl or a heterocyclyl, transformation to the alkoxycarbonylethyl-group may be carried out by deoxygenation, e.g. by hydrogenolysis in presence of a catalyst such as Pd/C, or by treatment with a reducing agent such as e.g. $BH_3.Me_2S$ or $Et_3Si$—H optionally in presence of an acid or Lewis acid such as e.g. TFA or $BF_3.OEt_2$. Alternatively the transformation to the alkoxycarbonylethyl-group may be carried out by 1,2-elimination (e.g. promoted by treatment with $Tf_2O$ in presence of a base such as DIPEA) and subsequent hydrogenation of the alkene intermediate. Such an alkene intermediate may also be prepared directly starting from the formyl-derivative using Wittig-, Wittig-Horner-, Wadsworth-Emmons-, or Peterson-type olefinations. Procedures for such olefinations are found in large numbers in literature and are commonly known to those skilled in the art.

Prior to the derivatizations of the functional group on $R^6$, sensitive functional groups 3a/b may be suitably protected (e.g. silylation of a hydroxy group) and deprotected again when desired or required (as described e.g. in "Protective Groups in Organic Synthesis" by T. W. Greene and P. G. M. Wuts, $2^{nd}$ Ed., 1991, Wiley N.Y.).

The conversion of a compound of formula (I) into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula (I) by treatment with physiologically compatible bases.

The conversion of compounds of formula (I) into pharmaceutically acceptable esters can be carried out e.g. by treatment of suited amino or hydroxy groups present in the molecules with an carboxylic acid such as acetic acid, with a condensating reagent such as benzotriazol-1-yloxytris(dimethylamino)phosphonium hexafluorophosphate (BOP) or N,N-dicylohexylcarbodiimide (DCCI) to produce the carboxylic ester or carboxylic amide.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment and prophylaxis of age-related and inherited (e.g. Stargardt's disease) forms of macular degeneration.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by LXR alpha and/or LXR beta agonists, particularly as therapeutically active substances for the treatment and/or prophylaxis of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease.

In another preferred embodiment, the invention relates to a method for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease, which method comprises administering a compound as defined above to a human being or animal.

The invention also embraces the use of compounds as defined above for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease.

The invention also relates to the use of compounds as described above for the preparation of medicaments for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease. Such medicaments comprise a compound as described above.

Prevention and/or treatment of increased lipid levels, increased cholesterol levels, atherosclerotic diseases, dyslipidemia, or diabetes is the preferred indication, particularly prevention and/or treatment of increased lipid levels, increased cholesterol levels, atherosclerotic diseases, or dyslipidemia, especially prevention and/or treatment of atherosclerotic diseases or dyslipidemia.

The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXR alpha and LXR beta. Bacterial expression vectors were constructed to produce glutathione-s-transferase (GST) fused to the ligand binding domains (LBD) of human LXR alpha (aa 164 to 447) and human LXR beta (aa 155 to 460). To accomplish this, the portions of the sequences encoding the LBDs were amplified from full-length clones by PCR and then subcloned into the plasmid vectors. Final clones were verified by DNA sequence analysis (Willy et al., Genes Dev. 1995, 9:1033-45; Song et al., Proc Natl Acad Sci USA. 1994, 91:10809-13).

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al).

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Abbreviations $Ac_2O$=acetic anhydride, $CH_2Cl_2$=dichloromethane, $^tBuOH$=tert-butanol, DBU=1,8-diazabicyclo[5.4.0]undec-7-ene, DIPEA N-ethyl diisopropylamine, DMF=dimethylformamide, EDCI=N-(3-dimethylaminopropyl)-N'-ethylcarbodiimide hydrochloride, EtOAc=ethylacetate, EtOH=ethanol, $Et_2O$=diethylether, eq=equivalent, HCl=hydrochloric acid, HOBT=1-hydroxybenzotriazole, MeOH=methanol, $NH_4Cl$=ammonium chloride, NaOH=sodium hydroxide, NaOMe=sodium methoxide, NCS=N-chlorosuccinimide, RT=room temperature, TBAF=tetrabutyl ammonium fluoride, TFAA=trifluoroacetic anhydride, TESCl=chlorotriethylsilane, THF=tetrahydrofurane.

General Remarks

All reactions were performed under argon.

Example 1

2-[4-(benzyl-ethyl-amino)-phenyl]-1,1,1,3,3,3-hexafluoro-propan-2-ol 1.1

A solution of 5 g (19.3 mmol) of 2-(4-amino-phenyl)-1,1,1,3,3,3-hexafluoro-propan-2-ol in 25 mL of pyridine was treated with 2.2 mL (23.3 mmol) of $Ac_2O$. The mixture was stirred at 60° C. for 2 hours and the solvent partially evaporated. The residue was distributed between a diluted aqueous solution of HCl and $Et_2O$. The combined organic phases were dried over $Na_2SO_4$ and evaporated to yield 5.7 g of crude N-[4-(2,2,2-trifluoro-1-hydroxy-1-trifluoromethyl-ethyl)-phenyl]-acetamide that was dissolved in 100 mL of DMF, treated with 3.4 mL (22.7 mmol) of DBU and then dropwise at 0° C. with 3.8 mL (22.7 mmol) of TESCl. The mixture was stirred at RT for 10 hours and then poured into a saturated aqueous solution of $NH_4Cl$ and $Et_2O$. The phases were separated and the aqueous one was extracted with $Et_2O$. The combined organic phases were dried over $Na_2SO_4$ and evaporated to yield 8.3 g of crude N-[4-(2,2,2-trifluoro-1-triethylsilanyloxy-1-trifluoromethyl-ethyl)-phenyl]-acetamide which was dissolved in 100 mL of THF and treated with 3.4 mL of a 1M $BH_3$*THF-solution in THF. The mixture was kept at reflux for 4 hours and the solvent partially evaporated. After addition of a saturated aqueous solution of $NH_4Cl$ and $Et_2O$, the phases were separated and the aqueous one was extracted with $Et_2O$. The combined organic phases were dried over $Na_2SO_4$ and evaporated. Column chromatography on silica gel with n-heptane/EtOAc 9:1 yielded 7.5 g (96%) of ethyl-[4-(2,2,2-trifluoro-1-triethylsilanyloxy-1-trifluoromethyl-ethyl)-phenyl]-amine, light yellow oil, MS: 402 ($MH^+$).

1.2

To a solution of 0.5 g (1.24 mmol) of ethyl-[4-(2,2,2-trifluoro-1-triethylsilanyloxy-1-trifluoromethyl-ethyl)-phenyl]-amine in 2 mL of DMF were added 0.3 mL (2.5 mmol) of benzylbromide and the mixture was stirred overnight at 80° C. After distribution between a 2M aqueous solution of NaOH and $Et_2O$, drying of the combined organic phases over $Na_2SO_4$ and evaporation, the resulting crude was dissolved in 5 mL of MeOH, treated with 1 mL of a 2M NaOMe-solution in MeOH and stirred for 30 min. Evaporation of the solvent and column chromatography on silica gel with n-heptane/EtOAc 95:5 gave 0.33 g (70%) of 2-[4-(benzyl-ethyl-amino)-phenyl]-1,1,1,3,3,3-hexafluoro-propan-2-ol, light yellow semi-solid, MS: 378 ($MH^+$).

Example 2

2-{4-[(2-chloro-benzyl)-ethyl-amino]-phenyl}-1,1,1,3,3,3-hexafluoro-propan-2-ol

In analogy to example 1.2, from ethyl-[4-(2,2,2-trifluoro-1-triethylsilanyloxy-1-trifluoromethyl-ethyl)-phenyl]-amine and 1-chloro-2-chloromethyl-benzene was prepared 2-{4-[(2-chloro-benzyl)-ethyl-amino]-phenyl}-1,1,1,3,3,3-hexafluoro-propan-2-ol, light yellow oil, MS: 412 ($MH^+$, 1Cl).

Example 3

2-{4-[(3-chloro-benzyl)-ethyl-amino]-phenyl}-1,1,1,3,3,3-hexafluoro-propan-2-ol

In analogy to example 1.2, from ethyl-[4-(2,2,2-trifluoro-1-triethylsilanyloxy-1-trifluoromethyl-ethyl)-phenyl]-amine and 1-chloro-3-chloromethyl-benzene was prepared 2-{4-[(3-chloro-benzyl)-ethyl-amino]-phenyl}-1,1,1,3,3,3-hexafluoro-propan-2-ol, light yellow oil, MS: 412 ($MH^+$, 1Cl).

Example 4

2-{4-[(4-chloro-benzyl)-ethyl-amino]-phenyl}-1,1,1,3,3,3-hexafluoro-propan-2-ol

In analogy to example 1.2, from ethyl-[4-(2,2,2-trifluoro-1-triethylsilanyloxy-1-trifluoromethyl-ethyl)-phenyl]-amine and 1-chloro-4-chloromethyl-benzene was prepared 2-{4-

[(4-chloro-benzyl)-ethyl-amino]-phenyl}-1,1,1,3,3,3-hexafluoro-propan-2-ol, light yellow oil, MS: 412 (MH+, 1Cl).

Example 5

2-[4-(ethyl-phenethyl-amino)-phenyl]-1,1,1,3,3,3-hexafluoro-propan-2-ol

In analogy to example 1.2, from ethyl-[4-(2,2,2-trifluoro-1-triethylsilanyloxy-1-trifluoromethyl-ethyl)-phenyl]-amine and 2-phenyl ethylbromide was prepared 2-[4-(ethyl-phenethyl-amino)-phenyl]-1,1,1,3,3,3-hexafluoro-propan-2-ol, light yellow oil, MS: 392 (MH+).

Example 6

2-[4-(benzhydryl-ethyl-amino)-phenyl]-1,1,1,3,3,3-hexafluoro-propan-2-ol

In analogy to example 1.2, from ethyl-[4-(2,2,2-trifluoro-1-triethylsilanyloxy-1-trifluoromethyl-ethyl)-phenyl]-amine and bromodiphenylmethane was prepared 2-[4-(benzhydryl-ethyl-amino)-phenyl]-1,1,1,3,3,3-hexafluoro-propan-2-ol, pink oil, MS: 454 (MH+).

Example 7

2-{4-[ethyl-(thiazol-4-ylmethyl)-amino]-phenyl}-1,1,1,3,3,3-hexafluoro-propan-2-ol In analogy to example 1.2, from ethyl-[4-(2,2,2-trifluoro-1-triethylsilanyloxy-1-trifluoromethyl-ethyl)-phenyl]-amine and 4-chloromethyl-thiazole was prepared 2-{4-[ethyl-(thiazol-4-ylmethyl)-amino]-phenyl}-1,1,1,3,3,3-hexafluoro-propan-2-ol, light brown oil, MS: 385 (MH+).

Example 8

2-{4-[ethyl-(pyridin-2-ylmethyl)-amino]-phenyl}-1,1,1,3,3,3-hexafluoro-propan-2-ol In analogy to example 1.2, from ethyl-[4-(2,2,2-trifluoro-1-triethylsilanyloxy-1-trifluoromethyl-ethyl)-phenyl]-amine and 2-bromomethyl-pyridine hydrobromide was prepared 2-{4-[ethyl-(pyridin-2-ylmethyl)-amino]-phenyl}-1,1,1,3,3,3-hexafluoro-propan-2-ol, white solid, MS: 379 (MH+).

Example 9

2-{4-[ethyl-(pyridin-3-ylmethyl)-amino]-phenyl}-1,1,1,3,3,3-hexafluoro-propan-2-ol In analogy to example 1.2, from ethyl-[4-(2,2,2-trifluoro-1-triethylsilanyloxy-1-trifluoromethyl-ethyl)-phenyl]-amine and 3-bromomethyl-pyridine hydrochloride was prepared 2-{4-[ethyl-(pyridin-3-ylmethyl)-amino]-phenyl}-1,1,1,3,3,3-hexafluoro-propan-2-ol, light brown oil, MS: 379 (MH+).

Example 10

2-{4-[ethyl-(pyridin-4-ylmethyl)-amino]-phenyl}-1,1,1,3,3,3-hexafluoro-propan-2-ol In analogy to example 1.2, from ethyl-[4-(2,2,2-trifluoro-1-triethylsilanyloxy-1-trifluoromethyl-ethyl)-phenyl]-amine and 4-bromomethyl-pyridine hydrochloride was prepared 2-{4-[ethyl-(pyridin-4-ylmethyl)-amino]-phenyl}-1,1,1,3,3,3-hexafluoro-propan-2-ol, light brown oil, MS: 379 (MH+).

Example 11

2-{4-[benzyl-(2,2,2-trifluoro-ethyl)-amino]-phenyl}-1,1,1,3,3,3-hexafluoro-propan-2-ol 11.1

A solution of 3.0 g (11.6 mmol) of 2-(4-amino-phenyl)-1,1,1,3,3,3-hexafluoro-propan-2-ol in 40 mL of $CH_2Cl_2$ was treated with 3.0 mL (17.4 mmol) of DIPEA and dropwise at 0° with 1.8 mL (12.9 mmol) of TFAA. After stirring 1 hour at RT the mixture was distributed between a saturated aqueous solution of $NH_4Cl$ and $Et_2O$. The combined organic phases were dried over $Na_2SO_4$ and evaporated to yield 4.2 g (quantitative) of crude 2,2,2-trifluoro-N-[4-(2,2,2-trifluoro-1-hydroxy-1-trifluoromethyl-ethyl)-phenyl]-acetamide, light brown oil, MS: 356 (MH+).

11.2

A solution of 4.2 g (11.8 mmol) of 2,2,2-trifluoro-N-[4-(2,2,2-trifluoro-1-hydroxy-1-trifluoromethyl-ethyl)-phenyl]-acetamide in 30 mL of THF was treated with 24.2 mL of a 1M $BH_3$.THF-complex solution in THF. The mixture was stirred for 72 hours at RT and then refluxed for 2 hours. After cooling to RT, the mixture was distributed between a saturated aqueous solution of $NH_4Cl$ and $Et_2O$. The combined organic phases were dried over $Na_2SO_4$ and evaporated. Column chromatography on silicagel with n-heptane/EtOAc 4:1 yielded 3.0 g (74%) of 1,1,1,3,3,3-hexafluoro-2-[4-(2,2,2-trifluoro-ethylamino)-phenyl]-propan-2-ol, light brown oil, MS: 342 (MH+).

11.3

A solution of 100 mg (0.29 mmol) of 1,1,1,3,3,3-hexafluoro-2-[4-(2,2,2-trifluoro-ethylamino)-phenyl]-propan-2-ol in 0.5 mL $^tBuOH$ was treated with 0.1 mL (0.84 mmol) of benzylbromide and stirred at 100° C. for 10 hours in a sealed tube. Evaporation of the solvent and column chromatography on silicagel with n-heptane/EtOAc 8:1 yielded 10 mg (8%) of 2-{4-[benzyl-(2,2,2-trifluoro-ethyl)-amino]-phenyl}-1,1,1,3,3,3-hexafluoro-propan-2-ol, blue oil, MS: 432 (MH+).

Example 12

2-{4-[(5-chloro-benzo[b]thiophen-2-ylmethyl)-(2,2,2-trifluoro-ethyl)-amino]-phenyl}-1,1,1,3,3,3-hexafluoro-propan-2-ol A solution of 100 mg (0.29 mmol) of 1,1,1,3,3,3-hexafluoro-2-[4-(2,2,2-trifluoro-ethylamino)-phenyl]-propan-2-ol (example 11.2) in 0.5 mL $^tBuOH$ was treated with 115 mg (0.44 mmol) of 5-chloro-2-chloromethyl-benzo[b]thiophene and stirred at 120° C. for 10 hours in a sealed tube. Evaporation of the solvent and column chromatography on silicagel with n-heptane/EtOAc 8:1 yielded 30 mg (19%) of 2-{4-[(5-chloro-benzo[b]thiophen-2-ylmethyl)-(2,2,2-trifluoro-ethyl)-amino]-phenyl}-1,1,1,3,3,3-hexafluoro-propan-2-ol, light yellow oil, MS: 520 ((M-H)−, 1Cl).

Example 13

2-{4-[ethyl-(2-hydroxy-2-phenyl-ethyl)-amino]-phenyl}-1,1,1,3,3,3-hexafluoro-propan-2-ol 13.1

A solution of 4 g (10 mmol) of ethyl-[4-(2,2,2-trifluoro-1-triethylsilanyloxy-1-trifluoromethyl-ethyl)-phenyl]-amine (example 1.1) in 12 mL of acetonitrile was treated with 2.3 mL (20 mmol) of racemic phenyloxirane and 2.12 g (20 mmol) of lithiumperchlorate. The mixture was stirred overnight at 80° C. in a sealed tube. The crude was distributed between saturated aqueous $NH_4Cl$ and $Et_2O$ and the combined organic phases were dried over $Na_2SO_4$ and evaporated. Column chromatography on silica gel with n-heptane/EtOAc 9:1 yielded 3.5 g (66%) of 2-{ethyl-[4-(2,2,2-trifluoro-1-triethylsilanyloxy-1-trifluoromethyl-ethyl)-phenyl]-amino}-2-phenyl-ethanol, light yellow oil, MS: 522 ($MH^+$) and 0.475 g (9%) of 2-{ethyl-[4-(2,2,2-trifluoro-1-triethylsilanyloxy-1-trifluoromethyl-ethyl)-phenyl]-amino}-1-phenyl-ethanol, light yellow oil, MS: 522 ($MH^+$).

13.2

A solution of 300 mg (0.58 mmol) of 2-{ethyl-[4-(2,2,2-trifluoro-1-triethylsilanyloxy-1-trifluoromethyl-ethyl)-phenyl]-amino}-1-phenyl-ethanol in 7.5 mL of THF was treated with 1.5 mL of a 1M TBAF-solution in THF and stirred at RT for 1 hour. Evaporation of the solvent and column chromatography on silica gel with n-heptane/EtOAc 9:1 yielded 153 mg (65%) of 2-{4-[ethyl-(2-hydroxy-2-phenyl-ethyl)-amino]-phenyl}-1,1,1,3,3,3-hexafluoro-propan-2-ol, white solid, MS: 408 ($MH^+$).

Example 14

(R)2-{4-[ethyl-(2-hydroxy-2-phenyl-ethyl)-amino]-phenyl}-1,1,1,3,3,3-hexafluoro-propan-2

In analogy to example 13, from ethyl-[4-(2,2,2-trifluoro-1-triethylsilanyloxy-1-trifluoromethyl-ethyl)-phenyl]-amine and (S) phenyloxirane was prepared (R)2-{4-[ethyl-(2-hydroxy-2-phenyl-ethyl)-amino]-phenyl}-1,1,1,3,3,3-hexafluoro-propan-2-ol, light yellow oil, MS: 408 ($MH^+$).

Example 15

(S)2-{4-[ethyl-(2-hydroxy-2-phenyl-ethyl)-amino]-phenyl}-1,1,1,3,3,3-hexafluoro-propan-2-ol In analogy to example 13, from ethyl-[4-(2,2,2-trifluoro-1-triethylsilanyloxy-1-trifluoromethyl-ethyl)-phenyl]-amine and (R) phenyloxirane was prepared (S)2-{4-[ethyl-(2-hydroxy-2-phenyl-ethyl)-amino]-phenyl}-1,1,1,3,3,3-hexafluoro-propan-2-ol, light yellow oil, MS: 408 ($MH^+$).

Example 16

(R)2-(4-{[2-(3-chloro-phenyl)-2-hydroxy-ethyl]-ethyl-amino}-phenyl)-1,1,1,3,3,3-hexafluoro-propan-2-ol In analogy to example 13, from ethyl-[4-(2,2,2-trifluoro-1-triethylsilanyloxy-1-trifluoromethyl-ethyl)-phenyl]-amine and (S) (3-chloro-phenyl)oxirane was prepared (R)2-(4-{[2-(3-chloro-phenyl)-2-hydroxy-ethyl]-ethyl-amino}-phenyl)-1,1,1,3,3,3-hexafluoro-propan-2-ol, yellow oil, MS: 440 ($(M-H)^-$, 1Cl).

Example 17

2-[4-(benzyl-ethyl-amino)-3-chloro-phenyl]-1,1,1,3,3,3-hexafluoro-propan-2-ol

A solution of 20 mg (0.05 mmol) of 2-[4-(benzyl-ethyl-amino)-phenyl]-1,1,1,3,3,3-hexafluoro-propan-2-ol (example 1.2) in 0.5 mL of 2-propanol was treated with 7 mg (0.05 mmol) of NCS. The mixture was stirred at 80° C. for 10 hours and the solvent was evaporated. Column chromatography on silicagel with n-heptane/EtOAc 9:1 yielded 17 mg (82%) of 2-[4-(benzyl-ethyl-amino)-3-chloro-phenyl]-1,1,1,3,3,3-hexafluoro-propan-2-ol, colorless oil, MS: 412 ($MH^+$, 1Cl).

Example 18

2-{3-chloro-4-[ethyl-(thiazol-4-ylmethyl)-amino]-phenyl}-1,1,1,3,3,3-hexafluoro-propan-2-ol In analogy to example 17, from 2-{4-[ethyl-(thiazol-4-ylmethyl)-amino]-phenyl}-1,1,1,3,3,3-hexafluoro-propan-2-ol (example 7) was prepared 2-{3-chloro-4-[ethyl-(thiazol-4-ylmethyl)-amino]-phenyl}-1,1,1,3,3,3-hexafluoro-propan-2-ol, light brown solid, MS: 419 ($MH^+$, 1Cl).

Example 19

2-{4-[benzyl-(2,2,2-trifluoro-ethyl)-amino]-3-chloro-phenyl}-1,1,1,3,3,3-hexafluoro-propan-2-ol In analogy to example 17, from 2-{4-[benzyl-(2,2,2-trifluoro-ethyl)-amino]-phenyl}-1,1,1,3,3,3-hexafluoro-propan-2-ol (example 11.3) was prepared 2-{4-[benzyl-(2,2,2-trifluoro-ethyl)-amino]-3-chloro-phenyl}-1,1,1,3,3,3-hexafluoro-propan-2-ol, light yellow oil, MS: 466 ($MH^+$, 1Cl).

Example 20

2-{3-chloro-4-[ethyl-(3-phenyl-propyl)-amino]-phenyl}-1,1,1,3,3,3-hexafluoro-propan-2-ol 20.1

In analogy to example 17, from 2-(4-aminophenyl)-1,1,1,3,3,3-hexafluoro-propan-2-ol was prepared 2-(4-amino-3-chloro-phenyl)-1,1,1,3,3,3-hexafluoro-propan-2-ol, light brown solid, MS: 292 ($(M-H)^-$, 1Cl).

20.2

A solution of 1 g (3.4 mmol) of 2-(4-amino-3-chloro-phenyl)-1,1,1,3,3,3-hexafluoro-propan-2-ol in 5 mL of pyridine was treated with 0.42 mL (4.4 mmol) of $Ac_2O$ and stirred at 70° C. for 10 hours. The solvent was evaporated, the residue dissolved in THF, treated with a 2M aqueous solution of NaOH and stirred for 1 h at RT. After acidification of the mixture to a pH of ca. 7 by adding aqueous HCl, $Et_2O$ and $H_2O$ were added, the phases were separated and the aqueous one was extracted with $Et_2O$. The combined organic phases were dried over $Na_2SO_4$ and evaporated to yield 1.1 g (ca. 94%) of crude N-[2-chloro-4-(2,2,2-trifluoro-1-hydroxy-1-trifluoromethyl-ethyl)-phenyl]-acetamide, which was dissolved in 20 mL of DMF and treated with 0.65 mL (4.37 mmol) of DBU and then at 0° C. dropwise with 0.73 mL (4.37 mmol) of TESCl. The mixture was stirred overnight and poured into a mixture of a saturated aqueous solution of $NH_4Cl$ and $Et_2O$. The phases were separated and the aqueous one extracted with Et$_2$O. The combined organic phases were dried over Na$_2$SO$_4$ and evaporated to yield 1.53 g (93%) of crude N-[2-chloro-4-(2,2,2-trifluoro-1-triethylsilanyloxy-1-trifluoromethyl-ethyl)-phenyl]-acetamide, yellow oil, MS: 450 (MH$^+$, 1Cl).

20.3

A solution of 1.54 g (3.42 mmol) of crude N-[2-chloro-4-(2,2,2-trifluoro-1-triethylsilanyloxy-1-trifluoromethyl-ethyl)-phenyl]-acetamide in 20 mL of THF was treated with 6.85 mL of a 1M solution of BH$_3$.THF-complex in THF. The mixture was kept at reflux for 3 hours and the solvent evaporated. The residue was distributed between a saturated aqueous solution of NH$_4$Cl and Et$_2$O. The combined organic phases were dried over Na$_2$SO$_4$ and the solvent was evaporated. Column chromatography on silica gel with n-heptane/EtOAc 95:5 yielded 0.922 g (61%) of [2-chloro-4-(2,2,2-trifluoro-1-triethylsilanyloxy-1-trifluoromethyl-ethyl)-phenyl]-N-ethyl-amine, colorless liquid, MS: 436 (MH$^+$, 1Cl).

20.4

A solution of 100 mg (0.23 mmol) of [2-chloro-4-(2,2,2-trifluoro-1-triethylsilanyloxy-1-trifluoromethyl-ethyl)-phenyl]-N-ethyl-amine in CH$_2$Cl$_2$ was treated with 0.08 mL (0.46 mmol) of DIPEA and 0.07 mL (0.46 mmol) of 3-phenylpropionylchloride. The mixture was stirred at RT for 10 hours and treated with 0.4 mL of a 1 M TBAF-solution in THF. Evaporation of the solvent and column chromatography on silica gel with n-heptane/EtOAc 4:1 yielded 70 mg (67%) of N-[2-chloro-4-(2,2,2-trifluoro-1-hydroxy-1-trifluoromethyl-ethyl)-phenyl]-N-ethyl-3-phenyl-propionamide, light yellow oil, MS: 454 (MH$^+$, 1Cl).

20.5

A solution of 70 mg (0.15 mmol) of N-[2-chloro-4-(2,2,2-trifluoro-1-hydroxy-1-trifluoromethyl-ethyl)-phenyl]-N-ethyl-3-phenyl-propionamide in 3 mL of THF was treated with 1 mL of 1M BH$_3$.THF-complex in THF and stirred for 10 hours at 80° C. in a sealed tube. Evaporation of the solvent and column chromatography on silica gel with CH$_2$Cl$_2$/n-heptane 1:1 yielded 60 mg (91%) of 2-{3-chloro-4-[ethyl-(3-phenyl-propyl)-amino]-phenyl}-1,1,1,3,3,3-hexafluoro-propan-2-ol, colorless oil, MS: 440 (MH$^+$, 1Cl).

Example 21

2-[3-chloro-4-(ethyl-phenethyl-amino)-phenyl]-1,1,1,3,3,3-hexafluoro-propan-2-ol 21.1

In analogy to example 20.4, from [2-chloro-4-(2,2,2-trifluoro-1-triethylsilanyloxy-1-trifluoromethyl-ethyl)-phenyl]-N-ethyl-amine and phenylacetyl chloride was prepared N-[2-chloro-4-(2,2,2-trifluoro-1-hydroxy-1-trifluoromethyl-ethyl)-phenyl]-N-ethyl-2-phenyl-acetamide, yellow gum, MS: 440 (MH$^+$, 1Cl).

21.2

In analogy to example 20.5, from N-[2-chloro-4-(2,2,2-trifluoro-1-hydroxy-1-trifluoromethyl-ethyl)-phenyl]-N-ethyl-2-phenyl-acetamide was prepared 2-[3-chloro-4-(ethyl-phenethyl-amino)-phenyl]-1,1,1,3,3,3-hexafluoro-propan-2-ol, colorless oil, MS: 426 (MH$^+$, 1Cl).

Example 22

1,1,1,3,3,3-hexafluoro-2-{4-[[5-methyl-2-(3-trifluoromethyl-phenyl)-oxazol-4-ylmethyl]-(2,2,2-trifluoro-ethyl)-amino]-phenyl}-propan-2-ol 22.1

4-chloromethyl-5-methyl-2-(3-trifluoromethyl-phenyl)-oxazole was prepared from 3-trifluoromethyl-benzaldehyde in analogy to the procedure described by Binggeli et al. (WO02/092084).

22.2

A mixture of 100 mg (0.29 mmol) of 1,1,1,3,3,3-hexafluoro-2-[4-(2,2,2-trifluoro-ethylamino)-phenyl]-propan-2-ol (example 11.2), of 81 mg (0.29 mmol) 4-chloromethyl-5-methyl-2-(3-trifluoromethyl-phenyl)-oxazole and ca 10 mg of NaI in DMF was stirred for 1 week at 125° C. and then distributed between a saturated aqueous solution of NH$_4$Cl and Et$_2$O. Drying of the combined organic phases over Na$_2$SO$_4$ and column chromatography on silica gel with a gradient of n-heptane/EtOAc gave 2 mg (ca. 1%) of 1,1,1,3,3,3-hexafluoro-2-{4-[[5-methyl-2-(3-trifluoromethyl-phenyl)-oxazol-4-ylmethyl]-(2,2,2-trifluoro-ethyl)-amino]-phenyl}-propan-2-ol, yellow solid, MS: 581 (MH$^+$).

Example 23

2-{4-[[2-(3-chloro-phenyl)-5-methyl-oxazol-4-ylmethyl]-(2,2,2-trifluoro-ethyl)-amino]-phenyl}-1,1,1,3,3,3-hexafluoro-propan-2-ol 23.1

4-chloromethyl-2-(3-chloro-phenyl)-5-methyl-oxazole was prepared from 3-chloro-benzaldehyde in analogy to the procedure described by Binggeli et al. (WO 02/092084).

23.2

In analogy to example 22.2, from 1,1,1,3,3,3-hexafluoro-2-[4-(2,2,2-trifluoro-ethylamino)-phenyl]-propan-2-ol and 4-chloromethyl-5-methyl-2-(3-chloro-phenyl)-oxazole was prepared 2-{4-[[2-(3-chloro-phenyl)-5-methyl-oxazol-4-ylmethyl]-(2,2,2-trifluoro-ethyl-amino]-phenyl}-1,1,1,3,3,3-hexafluoro-propan-2-ol, yellow solid, MS: 547 (MH$^+$, 1Cl).

Example 24

2-(4-{ethyl-[5-methyl-2-(3-trifluoromethyl-phenyl)-oxazol-4-ylmethyl]-amino}-phenyl)-1,1,1,3,3,3-hexafluoro-propan-2-ol 24.1

A solution of 1 g (3.86 mmol) of 2-(4-amino-phenyl)-1,1,1,3,3,3-hexafluoro-propan-2-ol in 2 ml of THF and 5 mL of pyridine was treated with 0.44 mL (4.63 mmol) of Ac$_2$O and stirred for 2 hrs at 60° C. The solvent was evaporated and the crude distributed between a diluted aqueous solution of HCl and Et$_2$O. the combined organic phases were dried over Na$_2$SO$_4$ and the solvent evaporated. The residue was dissolved in 5 mL of THF, treated with 7.7 mL of a 1M BH$_3$*THF-solution in THF and refluxed for 2 hrs. The solvent was evaporated and the residue distributed between a diluted aqueous solution of NaOH and Et$_2$O. The aqueous phase was then acidified by addition of an aqueous solution of HCl to a pH of ca. 7 and extracted with Et$_2$O. The combined organic phases were dried over Na$_2$SO$_4$ and the solvent evaporated to give 1.07 g (96%) of crude 2-(4-ethylamino-phenyl)-1,1,1,3,3,3-hexafluoro-propan-2-ol, light yellow solid, MS: 288 (MH+).

24.2

A solution of 100 mg (0.35 mmol) of 2-(4-ethylamino-phenyl)-1,1,1,3,3,3-hexafluoro-propan-2-ol and 96 mg (0.35 mmol) of 4-chloromethyl-5-methyl-2-(3-trifluoromethyl-phenyl)-oxazole (example 22.1) in 0.5 mL of DMF was stirred overnight at 80° C. After distribution of the crude mixture between a saturated aqueous solution of NH$_4$Cl and Et$_2$O, the combined organic phases were dried over Na$_2$SO$_4$ and the solvent was evaporated. Column chromatography on silica gel with toluene/EtOAc gave 91 mg (53%) of 2-(4-{ethyl-[5-methyl-2-(3-trifluoromethyl-phenyl)-oxazol-4-ylmethyl]-amino}-phenyl)-1,1,1,3,3,3-hexafluoro-propan-2-ol, yellow solid, MS: 527 (MH+).

Example 25

2-(4-{[2-(3-chloro-phenyl)-5-methyl-oxazol-4-ylmethyl]-ethyl-amino}-phenyl)-1,1,1,3,3,3-hexafluoro-propan-2-ol In analogy to example 24.2, from 2-(4-ethylamino-phenyl)-1,1,1,3,3,3-hexafluoro-propan-2-ol and 4-chloromethyl-5-methyl-2-(3-chloro-phenyl)-oxazole (example 23.1) was prepared 2-(4-{[2-(3-chloro-phenyl)-5-methyl-oxazol-4-ylmethyl]-ethyl-amino}-phenyl)-1,1,1,3,3,3-hexafluoro-propan-2-ol, orange solid, MS: 493 (MH+, 1Cl).

Example 26

2-(3-chloro-4-{ethyl-[5-methyl-2-(3-trifluoromethyl-phenyl)-oxazol-4-ylmethyl]-amino}-phenyl)-1,1,1,3,3,3-hexafluoro-propan-2-ol In analogy to example 17, from 2-(4-{ethyl-[5-methyl-2-(3-trifluoromethyl-phenyl)-oxazol-4-ylmethyl]-amino}-phenyl)-1,1,1,3,3,3-hexafluoro-propan-2-ol (example 24) was prepared 2-(3-chloro-4-{ethyl-[5-methyl-2-(3-trifluoromethyl-phenyl)-oxazol-4-ylmethyl]-amino}-phenyl)-1,1,1,3,3,3-hexafluoro-propan-2-ol, yellow gum, MS: 561 (MH+, 1Cl).

Example 27

2-(3-chloro-4-{[2-(3-chloro-phenyl)-5-methyl-oxazol-4-ylmethyl]-ethyl-amino}-phenyl)-1,1,1,3,3,3-hexafluoro-propan-2-ol In analogy to example 17, from prepared 2-(4-{[2-(3-chloro-phenyl)-5-methyl-oxazol-4-ylmethyl]-ethyl-amino}-phenyl)-1,1,1,3,3,3-hexafluoro-propan-2-ol (example 25) was prepared 2-(3-chloro-4-{[2-(3-chloro-phenyl)-5-methyl-oxazol-4-ylmethyl]-ethyl-amino}-phenyl)-1,1,1,3,3,3-hexafluoro-propan-2-ol, yellow waxy solid, MS: 527 (MH+, 2Cl).

Example 28

2-(4-{[2-(3-benzyloxy-phenyl)-5-methyl-oxazol-4-ylmethyl]-ethyl-amino}-phenyl)-1,1,1,3,3,3-hexafluoro-propan-2-ol 28.1

2-(3-benzyloxy-phenyl)-4-chloromethyl-5-methyl-oxazole was prepared from 3-benzyloxy-benzaldehyde in analogy to the procedure described by Binggeli et al. (WO 02/092084).

28.2

In analogy to example 24.2, from 2-(4-ethylamino-phenyl)-1,1,1,3,3,3-hexafluoro-propan-2-ol and 2-(3-benzyloxy-phenyl)-4-chloromethyl-5-methyl-oxazole was prepared 2-(4-{[2-(3-benzyloxy-phenyl)-5-methyl-oxazol-4-ylmethyl]-ethyl-amino}-phenyl)-1,1,1,3,3,3-hexafluoro-propan-2-ol, off-white solid, MS: 563 (M-H)−.

Example 29

2-(4-{[2-(4-benzyloxy-phenyl)-5-methyl-oxazol-4-ylmethyl]-ethyl-amino}-phenyl)-1,1,1,3,3,3-hexafluoro-propan-2-ol 29.1

2-(4-benzyloxy-phenyl)-4-chloromethyl-5-methyl-oxazole was prepared from 4-benzyloxy-benzaldehyde in analogy to the procedure described by Binggeli et al. (WO 02/092084).

29.2

In analogy to example 24.2, from 2-(4-ethylamino-phenyl)-1,1,1,3,3,3-hexafluoro-propan-2-ol and 2-(4-benzyloxy-phenyl)-4-chloromethyl-5-methyl-oxazole was prepared 2-(4-{[2-(4-benzyloxy-phenyl)-5-methyl-oxazol-4-ylmethyl]-ethyl-amino}-phenyl)-1,1,1,3,3,3-hexafluoro-propan-2-ol, light yellow solid, MS: 563 (M-H)−.

Example 30

3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid methyl ester 30.1

3-(4-chloromethyl-5-methyl-oxazol-2-yl)-benzoic acid methyl ester was prepared from 3-formyl-benzoic acid methyl ester in analogy to the procedure described by Binggeli et al. (WO 02/092084).

30.2

In analogy to example 24.2, from 2-(4-ethylamino-phenyl)-1,1,1,3,3,3-hexafluoro-propan-2-ol and 3-(4-chloromethyl-5-methyl-oxazol-2-yl)-benzoic acid methyl ester was prepared 3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid methyl ester, light yellow foam, MS: 515 (M-H)−.

Example 31

4-[4-({ethyl-[4-(2,2,2-trifluoro-1-hydroxy-1-trifluoromethyl-ethyl)-phenyl]-amino}-methyl)-5-methyl-oxazol-2-yl]-benzoic acid methyl ester 31.1

4-(4-chloromethyl-5-methyl-oxazol-2-yl)-benzoic acid methyl ester was prepared from 4-formyl-benzoic acid methyl ester in analogy to the procedure described by Binggeli et al. (WO 02/092084).

31.2

In analogy to example 24.2, from 2-(4-ethylamino-phenyl)-1,1,1,3,3,3-hexafluoro-propan-2-ol and 4-(4-chloromethyl-5-methyl-oxazol-2-yl)-benzoic acid methyl ester was prepared 4-[4-({ethyl-[4-(2,2,2-trifluoro-1-trifluoromethyl-ethyl)-phenyl]-amino}-methyl)-5-methyl-oxazol-2-yl]-benzoic acid methyl ester, light yellow foam, MS: 515 (M-H)⁻.

Example 32

3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid A solution of 92 mg (0.18 mmol) of 3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid methyl ester (example 30.2) in 1 mL of THF was treated with 1 mL of 1M aqueous LiOH and stirred at RT for 1 h. The mixture was acidified to pH 4-5 with aqueous HCl and distributed between Et₂O and H₂O. The combined organic phases were dried over Na₂SO₄ and evaporated to yield 79 mg (88%) of 3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid, light yellow solid, MS: 503 (MH⁺).

Example 33

4-[4-({ethyl-[4-(2,2,2-trifluoro-1-hydroxy-1-trifluoromethyl-ethyl)-phenyl]-amino}-methyl)-5-methyl-oxazol-2-yl]-benzoic acid In analogy to example 32, from 4-[4-({ethyl-[4-(2,2,2-trifluoro-1-hydroxy-1-trifluoromethyl-ethyl)-phenyl]-amino}-methyl)-5-methyl-oxazol-2-yl]-benzoic acid methyl ester (example 31.2) was prepared 4-[4-({ethyl-[4-(2,2,2-trifluoro-1-hydroxy-1-trifluoromethyl-ethyl)-phenyl]-amino}-methyl)-5-methyl-oxazol-2-yl]-benzoic acid, light yellow solid, MS: 503 (MH⁺).

Example 34

3-[4-({ethyl-[4-(2,2,2-trifluoro-1-hydroxy-1-trifluoromethyl-ethyl)-phenyl]-amino}-methyl)-5-methyl-oxazol-2-yl]-N-methyl-benzamide A solution of 22 mg (0.04 mmol) of 3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid (example 32) in 1 mL of DMF was treated with 9 mg (0.13 mmol) of methylamine hydrochloride and 0.03 mL (0.26 mmol) of 4-methylmorpholine and cooled to 0°. After addition of 12 mg (0.06 mmol) of EDCI and 1 mg (0.001 mmol) of HOBT the mixture was allowed to reach RT, stirred for 6 hours and distributed between Et₂O and a saturated aqueous solution of NH₄Cl. The combined organic phases were dried over Na₂SO₄ and evaporated. Column chromatography on silica gel with EtOAc gave 17 mg (75%) of 3-[4-({ethyl-[4-(2,2,2-trifluoro-1-hydroxy-1-trifluoromethyl-ethyl)-phenyl]-amino}-methyl)-5-methyl-oxazol-2-yl]-N-methyl-benzamide, colorless gum, MS: 516 (MH⁺).

Example 35

3-[4-({ethyl-[4-(2,2,2-trifluoro-1-hydroxy-1-trifluoromethyl-ethyl)-phenyl]-amino}-methyl)-5-methyl-oxazol-2-yl]-N,N-dimethyl-benzamide In analogy to example 34, from 3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid and dimethylamine hydrochloride was prepared 3-[4-({ethyl-[4-(2,2,2-trifluoro-1-hydroxy-1-trifluoromethyl-ethyl)-phenyl]-amino}-methyl)-5-methyl-oxazol-2-yl]-N,N-dimethyl-benzamide, colorless gum, MS: 530, (MH⁺).

Example 36

3-[4-({ethyl-[4-(2,2,2-trifluoro-1-hydroxy-1-trifluoromethyl-ethyl)-phenyl]-amino}-methyl)-5-methyl-oxazol-2-yl]-benzamide In analogy to example 34, from 3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid and ammonium chloride was prepared 3-[4-({ethyl-[4-(2,2,2-trifluoro-1-hydroxy-1-trifluoromethyl-ethyl)-phenyl]-amino}-methyl)-5-methyl-oxazol-2-yl]-benzamide, colorless gum, MS: 502, (MH⁺).

Example 37

4-[4-({ethyl-[4-(2,2,2-trifluoro-1-hydroxy-1-trifluoromethyl-ethyl)-phenyl]-amino}-methyl)-5-methyl-oxazol-2-yl]-N-methyl-benzamide In analogy to example 34, from 4-[4-({ethyl-[4-(2,2,2-trifluoro-1-hydroxy-1-trifluoromethyl-ethyl)-phenyl]-amino}-methyl)-5-methyl-oxazol-2-yl]-benzoic acid (example 33) and methylamine hydrochloride was prepared 4-[4-({ethyl-[4-(2,2,2-trifluoro-1-hydroxy-1-trifluoromethyl-ethyl)-phenyl]-amino}-methyl)-5-methyl-oxazol-2-yl]-N-methyl-benzamide, white solid, MS: 516 (MH⁺).

Example 38

4-[4-({ethyl-[4-(2,2,2-trifluoro-1-hydroxy-1-trifluoromethyl-ethyl)-phenyl]-amino}-methyl)-5-methyl-oxazol-2-yl]-N,N-dimethyl-benzamide In analogy to example 34, from 4-[4-({ethyl-[4-(2,2,2-trifluoro-1-hydroxy-1-trifluoromethyl-ethyl)-phenyl]-amino}-methyl)-5-methyl-oxazol-2-yl]-benzoic acid (example 33) and dimethylamine hydrochloride was prepared 4-[4-({ethyl-[4-(2,2,2-trifluoro-1-hydroxy-1-trifluoromethyl-ethyl)-phenyl]-amino}-methyl)-5-methyl-oxazol-2-yl]-N,N-dimethyl-benzamide, white solid, MS: 530 (MH⁺).

Example 39

4-[4-({ethyl-[4-(2,2,2-trifluoro-1-hydroxy-1-trifluoromethyl-ethyl)-phenyl]-amino}-methyl)-5-methyl-oxazol-2-yl]-benzamide In analogy to example 34, from 3-[4-({ethyl-[4-(2,2,2-trifluoro-1-hydroxy-1-trifluoromethyl-ethyl)-phenyl]-amino}-methyl)-5-methyl-oxazol-2-yl]-benzoic acid (example 33) and ammonium chloride was prepared 4-[4-({ethyl-[4-(2,2,2-trifluoro-1-hydroxy-1-trifluoromethyl-ethyl)-phenyl]-amino}-methyl)-5-methyl-oxazol-2-yl]-benzamide, white solid, MS: 502 (MH⁺).

Example 40

2-{4-[(2-benzyl-5-methyl-oxazol-4-ylmethyl)-ethyl-amino]-phenyl}-1,1,1,3,3,3-hexafluoro-propan-2-ol

40.1
2-Benzyl-4-chloromethyl-5-methyl-oxazole was prepared from phenyl-acetaldehyde in analogy to the procedure described by Binggeli et al. (WO 02/092084).

40.2
In analogy to example 24.2, from 2-(4-ethylamino-phenyl)-1,1,1,3,3,3-hexafluoro-propan-2-ol and 2-benzyl-4-chloromethyl-5-methyl-oxazole and 2-benzyl-4-chloromethyl-5-methyl-oxazole was prepared 2-{4-[(2-benzyl-5-methyl-oxazol-4-ylmethyl)-ethyl-amino]-phenyl}-1,1,1,3,3,3-hexafluoro-propan-2-ol, dark brown oil, MS: 473 (MH$^+$).

Example 41

2-{4-[ethyl-(5-methyl-2-((E)-styryl)-oxazol-4-ylmethyl)-amino]-phenyl}-1,1,1,3,3,3-hexafluoro-propan-2-ol

41.1
4-chloromethyl-5-methyl-2-((E)-styryl)-oxazole was prepared from (E)-3-phenyl-propenal in analogy to the procedure described by Binggeli et al (WO 02/092084).

41.2
In analogy to example 24.2, from 2-(4-ethylamino-phenyl)-1,1,1,3,3,3-hexafluoro-propan-2-ol and 4-chloromethyl-5-methyl-2-((E)-styryl)-oxazole and 4-chloromethyl-5-methyl-2-styryl-oxazole was prepared 2-{4-[ethyl-(5-methyl-2-((E)-styryl)-oxazol-4-ylmethyl)-amino]-phenyl}-1,1,1,3,3,3-hexafluoro-propan-2-ol, light yellow solid, MS: 485 (MH$^+$).

Example 42

2-{4-[ethyl-(5-methyl-2-phenethyl-oxazol-4-ylmethyl)-amino]-phenyl}-1,1,1,3,3,3-hexafluoro-propan-2-ol A solution of 40 mg (0.08 mmol) of 2-{4-[(2-benzyl-5-methyl-oxazol-4-ylmethyl)-ethyl-amino]-phenyl}-1,1,1,3,3,3-hexafluoro-propan-2-ol in 1 mL of MeOH was treated with 20 mg of Pd/C (10%) and hydrogenated at atmospheric pressure for 20 hours. Filtration and evaporation gave 25 mg (62%) of 2-{4-[ethyl-(5-methyl-2-phenethyl-oxazol-4-ylmethyl)-amino]-phenyl}-1,1,1,3,3,3-hexafluoro-propan-2-ol, light yellow oil, MS: 487 (MH$^+$).

Example 43

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxice (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesium stearate and compressed to yield kernels of 120 or 350 mg respectively. The kernels are lacquered with an aqueous solution/suspension of the above mentioned film coat.

Example 44

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 45

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 46

Soft gelatin capsules containing the following ingredients can be manufactured in a conventional manner:

Capsule Contents

| | |
|---|---|
| Compound of formula (I) | 5.0 mg |
| Yellow wax | 8.0 mg |

| | |
|---|---|
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 47

Sachets containing the following ingredients can be manufactured in a conventional manner:

| | |
|---|---|
| Compound of formula (I) | 50.0 mg |
| Lactose, fine powder | 1015.0 mg |
| Microcryistalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcryistalline cellulose and sodium carboxymethyl cellulose and granulated with a mixture of polyvinylpyrrolidone in water. The granulate is mixed with magnesium stearate and the flavouring additives and filled into sachets.

Example 48

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of GST-LXRα-LBD or 700 ng of GST-LXR beta-LBD fusion proteins were bound to 80 μg or 40 μg SPA beads (Pharmacia Amersham) respectively, in a final volume of 50 μl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 μl of buffer. Radioligand (eg. 100,000 dpm of (N-(2,2,2-trifluoroethyl)-N-[4-(2,2,2-trifluoro-1-hydroxy-1-trifluoromethyl-ethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6-well plates at a density of $10^5$ Cells/well and then batch-transfected with either the full-length-LXRα or full-length-LXRβ expression plasmids plus a reporter plasmid expressing luceriferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50) of 1 nM to 100 μM, preferably 1 nM to 10 μM, more preferably 1 nM to 1 μM.

For example, the following compounds showed the following IC50 values in the binding assay:

| Example | LXRalpha Binding IC50 [μmol/l] | LXRbeta Binding IC50 [μmol/l] |
|---|---|---|
| 1 | 0.046 | 0.031 |
| 18 | 0.017 | 0.0034 |
| 30 | 0.0027 | 0.0057 |

It is to be understood that the invention is not limited to the particular embodiments of the invention described above, as variations of the particular embodiments may be made and still fall within the scope of the appended claims.

What is claimed is:

1. A compound of the formula (I):

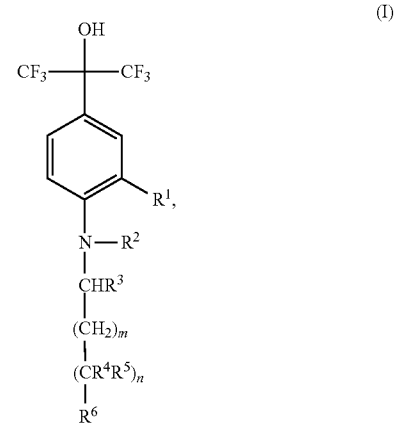

wherein:
R$^1$ is hydrogen, halogen, or lower-alkyl;
R$^2$ is ethyl or 2,2,2-trifluoro-ethyl;
R$^3$ is hydrogen, lower-alkyl, aryl, cycloalkyl, or heterocyclyl;

R⁴ is hydrogen, hydroxy, lower-alkoxy, aryl-lower-alkoxy, or heterocyclyl-lower-alkoxy;

R⁵ is hydrogen, lower-alkyl, aryl, or heterocyclyl;

R⁶ is aryl;

m is 0 to 3;

n is 0 or 1;

and pharmaceutically acceptable salts and esters thereof.

2. The compound according to claim 1, wherein R¹ is hydrogen or halogen.

3. The compound according to claim 1, wherein R¹ is hydrogen or chlorine.

4. The compound according to claim 1, wherein R³ is hydrogen or aryl.

5. The compound according to claim 1, wherein R³ is hydrogen or phenyl.

6. The compound according to claim 1, wherein R³ is hydrogen.

7. The compound according to claim 1, wherein R⁴ is hydrogen or hydroxy.

8. The compound according to claim 1, wherein R⁵ is hydrogen.

9. The compound according to claim 1, wherein R⁶ is phenyl.

10. The compound according to claim 1, wherein m is 0 to 2.

11. The compound according to claim 1, wherein m is 0.

12. The compound according to claim 1, wherein n is 0.

13. The compound according to claim 1, selected from the group consisting of:

2-[4-(Benzyl-ethyl-amino)-phenyl]-1,1,1,3,3,3-hexafluoro-propan-2-ol,

2-{4-[(2-Chloro-benzyl)-ethyl-amino]-phenyl}-1,1,1,3,3,3-hexafluoro-propan-2-ol, 2-{4-[(3-Chloro-benzyl)-ethyl-amino]-phenyl}-1,1,1,3,3,3-hexafluoro-propan-2-ol, 2-{4-[(4-Chloro-benzyl)-ethyl-amino]-phenyl}-1,1,1,3,3,3-hexafluoro-propan-2-ol, 2-[4-(Ethyl-phenethyl-amino)-phenyl]-1,1,1,3,3,3-hexafluoro-propan-2-ol, 2-{4-[Ethyl-(2-hydroxy-2-phenyl-ethyl)-amino]-phenyl}-1,1,1,3,3,3-hexafluoro-propan-2-ol, (R) 2-{4-[Ethyl-(2-hydroxy-2-phenyl-ethyl)-amino]-phenyl}-1,1,1,3,3,3-hexafluoro-propan-2-ol, (S) 2-{4-[Ethyl-(2-hydroxy-2-phenyl-ethyl)-amino]-phenyl}-1,1,1,3,3,3-hexafluoro-propan-2-ol, (R) 2-(4-{[2-(3-Chloro-phenyl)-2-hydroxy-ethyl]-ethyl-amino}-phenyl)-1,1,1,3,3,3-hexafluoro-propan-2-ol, 2-[4-(Benzyl-ethyl-amino)-3-chloro-phenyl]-1,1,1,3,3,3-hexafluoro-propan-2-ol, 2-{4-[Benzyl-(2,2,2-trifluoro-ethyl)-amino]-3-chloro-phenyl}-1,1,1,3,3,3-hexafluoro-propan-2-ol, 2-{3-Chloro-4-[ethyl-(3-phenyl-propyl)-amino]-phenyl}-1,1,1,3,3,3-hexafluoro-propan-2-ol, and 2-[3-Chloro-4-(ethyl-phenethyl-amino)-phenyl]-1,1,1,3,3,3-hexafluoro-propan-2-ol, and pharmaceutically acceptable salts and esters thereof.

14. The compound according to claim 1, selected from the group consisting of:

2-[4-(Benzyl-ethyl-amino)-3-chloro-phenyl]-1,1,1,3,3,3-hexafluoro-propan-2-ol, and 2-{4-[Benzyl-(2,2,2-trifluoro-ethyl)-amino]-3-chloro-phenyl}-1,1,1,3,3,3-hexafluoro-propan-2-ol, and pharmaceutically acceptable salts and esters thereof.

15. A pharmaceutical composition comprising a therapeutically effective amount of a compound according to claim 1 and a pharmaceutically acceptable carrier and/or adjuvant.

* * * * *